United States Patent
O'Connor (10) Patent No.: US 7,189,592 B2
(45) Date of Patent: Mar. 13, 2007

(54) MANUFACTURABLE SINGLE-CHIP HYDROGEN SENSOR

(75) Inventor: James M. O'Connor, Ellicott City, MD (US)

(73) Assignee: Honeywell International Inc., Morristown, NJ (US)

( * ) Notice: Subject to any disclaimer, the term of this patent is extended or adjusted under 35 U.S.C. 154(b) by 138 days.

(21) Appl. No.: 10/838,718

(22) Filed: May 3, 2004

(65) Prior Publication Data

US 2004/0206723 A1 Oct. 21, 2004

Related U.S. Application Data

(62) Division of application No. 09/788,781, filed on Feb. 20, 2001, now Pat. No. 6,730,270.

(60) Provisional application No. 60/183,602, filed on Feb. 18, 2000.

(51) Int. Cl.
- *G01N 27/00* (2006.01)
- *G01N 7/00* (2006.01)
- *G01N 30/96* (2006.01)
- *G01N 37/00* (2006.01)
- *G01N 9/00* (2006.01)

(52) U.S. Cl. .............. 438/49; 216/41; 422/83; 422/98; 73/1.01; 73/1.02; 436/43; 436/144; 436/149; 29/25.01; 29/592.1; 438/5; 438/48; 438/443; 438/494; 438/504; 438/664; 438/975

(58) Field of Classification Search ............ 422/83, 422/98; 216/41; 73/1.01, 1.02; 436/43, 436/144, 149; 29/592.1, 25.01; 438/48, 438/49, 5, 443, 494, 504, 664, 975
See application file for complete search history.

(56) References Cited

U.S. PATENT DOCUMENTS 6,450,007 B1 * 9/2002 O'Connor .............. 73/23.2

* cited by examiner

*Primary Examiner*—Brian Sines
(74) *Attorney, Agent, or Firm*—McDonnell Boehnen Hulbert & Berghoff LLP

(57) ABSTRACT

A robust single-chip hydrogen sensor and a method for fabricating such a sensor. By utilizing an interconnect metallization material that is the same or similar to the material used to sense hydrogen, or that is capable of withstanding an etchant used to pattern a hydrogen sensing portion, device yields are improved over prior techniques.

5 Claims, 6 Drawing Sheets

MANUFACTURABLE SINGLE-CHIP HYDROGEN SENSOR

PRIORITY

This application claims priority to and incorporates by reference U.S. Provisional Patent Application No. 60/183,602, entitled "Robust PdNi Hydrogen Sensor," filed on Feb. 18, 2000, and naming James M. O'Connor as an inventor. This application is a divisional of and also claims priority to Ser. No. 09/788,781, entitled "Manufacturable Single-Chip Hydrogen Sensor", filed Feb. 20, 2001, now U.S. Pat. No. 6,730,270 and also naming James M. O'Connor as an inventor.

FIELD

The present invention is related to hydrogen sensors, and more particularly, to a robust single-chip hydrogen sensor and method for manufacturing the same.

BACKGROUND

During the early 1990s, Sandia National Laboratory developed a single-chip hydrogen sensor that utilized Palladium-Nickel (PdNi) metal films as hydrogen gas sensors. U.S. Pat. No. 5,279,795, naming Robert C. Hughes and W. Kent Schubert as inventors, assigned to the United States as represented by the U.S. Department of Energy, describes such a sensor and is incorporated by reference herein.

One of the key benefits of the sensor described in the '795 patent is its ability to detect a dynamic range of hydrogen concentrations over at least six orders of magnitude. Prior solutions to the problem of detecting hydrogen concentrations had been generally limited to detecting low concentrations of hydrogen. These solutions include such technologies as metal-insulator-semiconductor (MIS) or metal-oxide-semiconductor (MOS) capacitors and field-effect-transistors (FET), as well as palladium-gated diodes.

The hydrogen sensor described in the '795 patent was a notable advance in hydrogen-sensing technology. It was, however, primarily limited to an experimental laboratory environment due to the difficulties encountered in manufacturing such a sensor.

In typical silicon fabrication facilities, metal films are first blanket-deposited across the entire wafer, and are subsequently patterned by an etch process. However, conventional etchants for PdNi also attack aluminum, which is normally present on the wafer surface as an interconnect metal before the PdNi film is deposited. Patterning the PDNI by etching would also attack the unprotected aluminum, destroying the sensor. Other non-conventional semiconductor fabrication techniques involving the use of a photoresistive material applied before the PdNi in a "lift-off" process have produced very low yields in tests performed by the assignee of the present invention. Low yields in the production of semiconductor devices typically translates to difficulties in producing a commercializable product.

One solution to the above problems is described in U.S. patent application Ser. No. 09/729,147, titled "Robust Single-Chip Hydrogen Sensor," assigned to Honeywell International Inc., and incorporated by reference herein. The technique disclosed is a lift-off process, in which an adhesion promoting layer, such as chromium, is provided to cause a sense-resistive layer, such as a PdNi layer, to adhere to an underlying base layer. As a result, during the lift-off process, there is a reduced likelihood of sensor portions being lifted off in conjunction with the portions actually intended to be removed. However, the use of chromium has been discovered to be prone to at least one disadvantage. The chromium has a tendency to affect the operation of hydrogen sensing transistors on the sensing chip. As a result, accuracy and/or sensing range may be affected.

It would thus be desirable to provide a robust single-chip hydrogen sensor that is capable of sensing hydrogen concentrations over a broad range, such as from approximately 1% to approximately 100% concentrations.

It would also be desirable for such a sensor to be efficiently manufacturable, so that costs are reduced and the sensor is producible in high enough yields to enable commercialization.

It would be desirable for such a sensor to provide measurement results that approximate or improve on the results from previous hydrogen sensors.

It would additionally be desirable to minimize sensor drift and to improve device-to-device and wafer-to-wafer repeatability.

SUMMARY

In accordance with an illustrative embodiment of the present invention, some of the problems associated with manufacturing a robust hydrogen sensor are addressed.

According to a first embodiment, a silicon-based hydrogen sensor is provided. The sensor includes at least one hydrogen sensing portion composed of a first material and at least one interconnect metallization also composed of the first material. The first material is preferably, but need not be, a palladium nickel alloy. The interconnect metallization is preferably covered with an oxide or nitride to make the interconnect metallization inert. In a first aspect of this embodiment, the hydrogen sensing portion and the interconnect metallization are formed concurrently with one another. In a second aspect of the invention, the sensor further includes an underlying layer and at least one contact between the interconnect metallization and the underlying layer. The underlying layer may, for example, be composed primarily of silicon, and the contact may be a silicided contact.

In a second embodiment, a silicon-based hydrogen sensor includes at least one hydrogen-sensing portion and at least one interconnect metallization. The hydrogen-sensing portion is patterned by a deposition, mask, and etch process, and the at least one interconnect metallization is composed of a material that is resistant to the deposition, mask, and etch process used to pattern the hydrogen-sensing portion. For example, the at least one hydrogen sensing portion may be composed of a palladium nickel alloy and the at least one interconnect metallization may be composed of a material that is relatively impervious to the hydrogen-sensing etch process, such as gold.

In a third embodiment, a method for fabricating a silicon-based hydrogen sensor is provided. The method includes providing an interconnect metallization and a hydrogen sensing portion made of the same material. The material is preferably a palladium nickel alloy. The interconnect metallization is preferably covered with an oxide or nitride to make the interconnect metallization inert. In another aspect of the invention, the method further includes providing a silicided contact between the interconnect metallization and an underlying base portion. The silicided contact may be provided by masking the underlying base portion, etching a contact portion from the masked underlying base portion, depositing a contact material, masking the contact material, and sintering the contact material. Exemplary materials that may be used to provide the contact include cobalt, titanium, tungsten, platinum, tantalum, and molybdenum.

In a fourth embodiment, a method for fabricating a single-chip hydrogen sensing-device is provided. The method includes forming a silicided contact on an underlying base portion, depositing a hydrogen sensing material over the silicided contact and the underlying base portion, masking a pattern in the hydrogen sensing material, and etching the hydrogen sensing material to form a hydrogen sensing portion and an interconnect metallization portion. In another aspect, the method may further include annealing the hydrogen sensing material. The interconnect metallization is preferably covered with an oxide or nitride to make the interconnect metallization inert. Forming the silicided contact may include depositing, etching, and sintering a first material, such as cobalt, titanium, tungsten, platinum, tantalum, and molybdenum.

BRIEF DESCRIPTION OF THE DRAWINGS

Presently preferred embodiments of the invention are described below in conjunction with the appended drawing figures, wherein like reference numerals refer to like elements in the various figures, and wherein.

DETAILED DESCRIPTION

Figure 1:
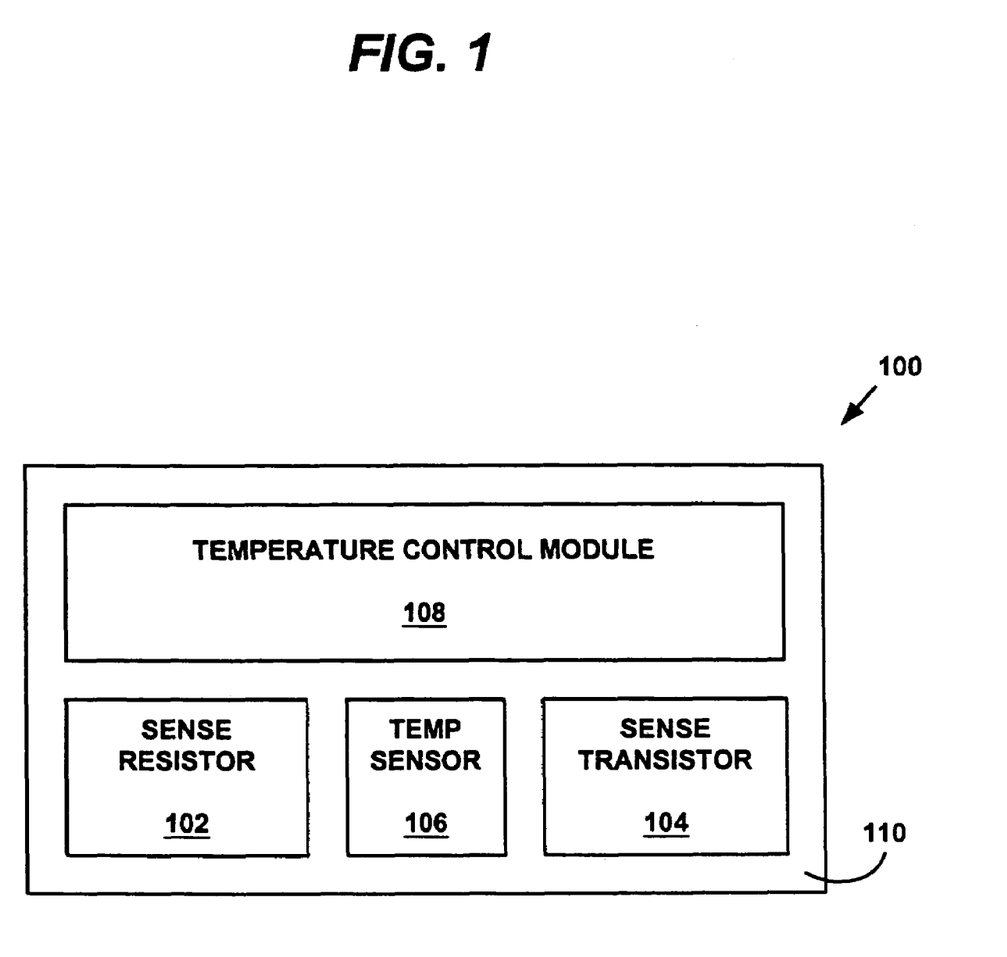
FIG. 1 is a simplified block diagram illustrating a robust single-chip hydrogen sensor according to an embodiment of the present invention.

FIG. 1 is a simplified block diagram illustrating a top view of a robust single-chip hydrogen sensor in accordance with an embodiment of the present invention. The sensor 100 includes at least one sense resistor 102, at least one sense transistor 104, at least one temperature sensor 106, and at least one temperature control module 108 located in or on a substrate 110. On-chip and/or external circuitry (not shown) may be included to assist in precisely regulating the temperature of the chip 100 using the temperature sensor 106 and the temperature control module 108. Similarly, the same external circuitry, or other external circuitry, may be used to obtain outputs from the sense resistor 102 and/or the sense transistor 104.

The substrate 110 preferably is a bulk silicon substrate. Silicon enables the use of many common silicon semiconductor processing techniques, such as masks, implants, etchings, dopings, and others.

The temperature control module 108 preferably includes one or more heater Field-Effect-Transistors (FETs) or other heating devices (for example, resistive heating elements) formed in or on the substrate 110. One or more cooling mechanisms may additionally or alternatively be included as part of the temperature control module 108. The temperature control module 108 adjusts the temperature of the sensor 100 in response to temperature measurements received from the temperature sensor 106 or associated external circuitry.

The temperature sensor 106 is preferably a temperature sensing diode formed in or on the substrate 110. Other methods for sensing temperature may also be used.

The sense transistor 104 is used to sense hydrogen concentration levels in an environment in which the sensor 100 is placed. The sense transistor 104 is preferably a PdNi-gate sense transistor that is fabricated in or on the substrate 110. Other types of sense transistors may also be used. The sense transistor 104 may utilize Metal-Oxide-Semiconductor (MOS) or Metal-Insulator-Semiconductor (MIS) technology. In an alternative embodiment, the sense transistor 104 may instead be a sensing element, such as a sense capacitor. (In such a case, alternating current measurement techniques may need to be employed.) The sense transistor 104 senses hydrogen concentration levels ranging from a first minimum concentration to a first maximum concentration. Typical values for the first minimum concentration and first maximum concentration are one part per million (ppm) and 1,000 ppm, respectively. Other minimum and maximum concentrations may also be possible for the sense transistor 104.

The sense resistor 102 is preferably a PdNi film arrayed in a serpentine pattern fabricated in or on the sensor 100. Other materials besides PdNi may be used, such as various palladium suicides and polymeric sensing elements. The resistance of the sense resistor 102 changes in the presence of hydrogen, enabling detection of hydrogen concentration in a particular environment. The sense resistor 102 is preferably operable to sense hydrogen levels ranging from a second minimum concentration to a second maximum concentration. Exemplary values for the second minimum concentration and second maximum concentration are 100 ppm and 1,000,000 ppm, respectively. Other minimums and maximums may also be possible.

Figure 2:
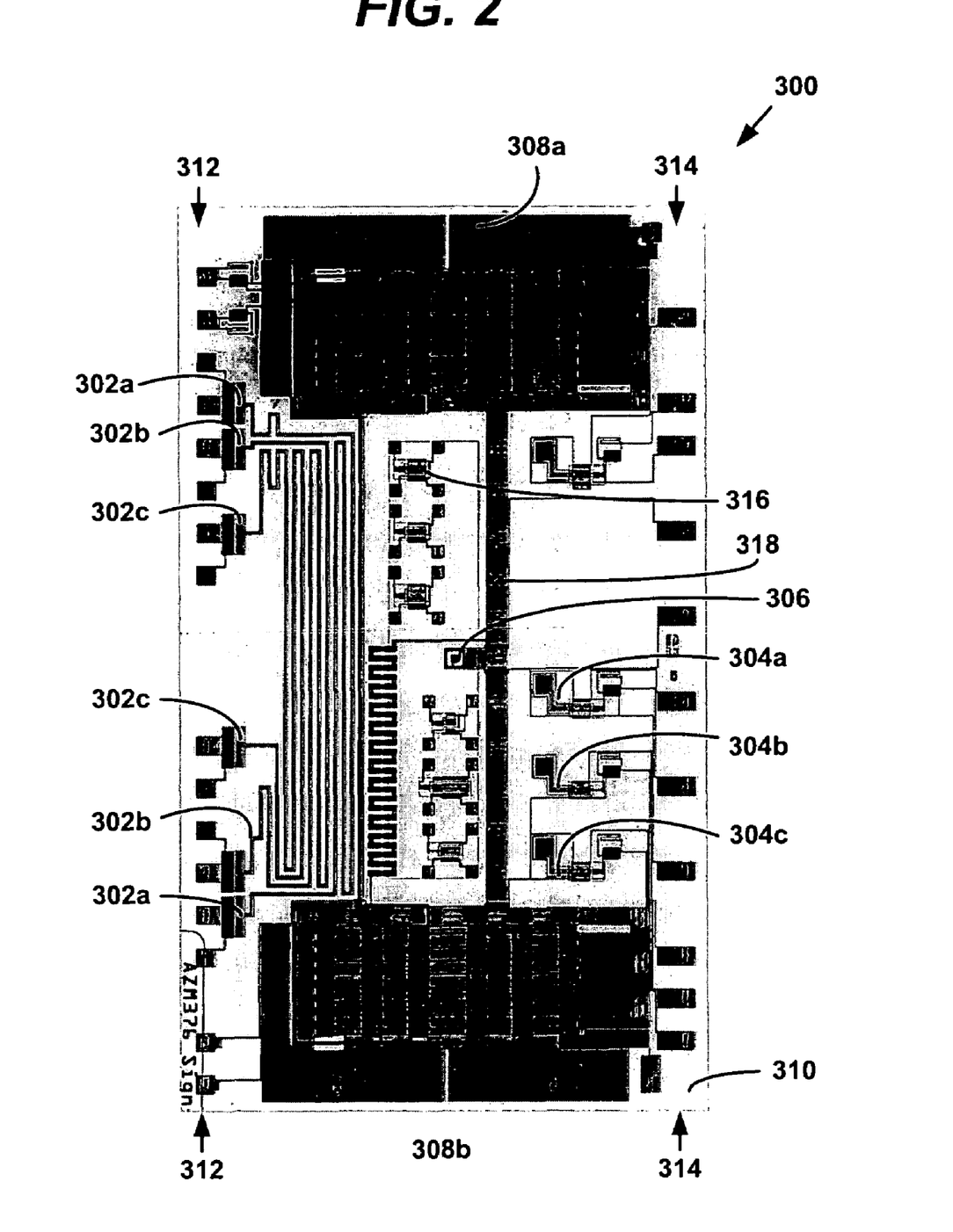
FIG. 2 is a block diagram illustrating a top view of a robust single-chip hydrogen sensor device according to a preferred embodiment of the present invention.

For purposes of illustration and to maintain generality, no connections are shown, and no external circuitry is shown in FIG. 1. Connections are likely to exist between the resistor 102, the sense transistor 104, the temperature sensor 106, the temperature control module 108, and/or any external circuitry. Such connections may be made by a network of interconnect metallizations, for example. In the preferred embodiment, the interconnect metallizations are formed of the same material as the sense transistor and/or the sense resistor. Thus, if the sense resistor and sensor transistor are composed of a PdNi alloy, an interconnect metallization is also composed of a PdNi alloy. When the interconnect metallization and hydrogen sensing portion are composed of the same material, the interconnect metallization is preferably covered with an oxide or nitride to render the interconnect metallization resistance unchanged in the presence of hydrogen. In another embodiment, the interconnect metallization is formed of any material that is capable of surviving a subtractive etch process. For example, gold or various alloys including gold, may be a suitable interconnect material for a hydrogen sensor. Further details on preferred connection layouts are shown in FIG. 2, described in further detail below.

Silicided contacts are preferably used to provide contacts to various components, such as the sources and drains of the sense transistor and the heater FET used in the temperature control module. Ideally, each silicided contact serves as an ohmic contact, such that the potential difference across the contact is proportional to the current passing through. Metals such as cobalt, titanium, tungsten, platinum, tantalum, and molybdenum, may be used to make silicided contacts. In an alternative embodiment, a silicide is also or alternatively used to implement all or a portion of the interconnect metallizations described above.

Also not shown in FIG. 1 is an underlying, non-conductive layer that may be used to isolate the sense resistor 102, the sense transistor 104, the temperature sensor 106, and/or the temperature control module 108 from the substrate 110. The non-conductive layer may, for example, be a silicon nitride or oxide layer. As used throughout this description, the term "non-conductive" is intended to describe conductive characteristics when compared to a conductive material, such as aluminum, or a semiconductive material, such as silicon. "Non-conductive" is not intended to imply an actual inability to conduct electricity regardless of applied conditions. Also, as used herein, the term "interconnect metallization" will typically refer to a material that is conductive with respect to any non-conductive layers.

Operation of the sensor 100 will now be briefly described. The temperature sensor 106 and temperature control module 108 are used to regulate the operating temperature of the sensor 100 when sensing hydrogen. The temperature of the sensor 100 may, for example, be held at a constant sense temperature. The temperature sensor 106 and temperature control module 108 may also be used to purge hydrogen and/or other gases, etc. after measurements are taken, by heating the chip to a purge temperature. In the preferred embodiment, the temperature control module 108 heats the chip to approximately 80 degrees Celsius, as measured at the temperature sensor 106. The purge temperature is preferably approximately 100 degrees Celsius. One or more feedback loops may be used to assist in accurately regulating the temperature using the temperature sensor 106 and the temperature control module 108. Such feedback loop(s) may be included in external circuitry, for example. When the sensor 100 is in a hydrogen-sensing mode, then the sense resistor 102 and the sense transistor 104 preferably sense hydrogen levels at overlapping ranges. This enables the combination of the sense resistor 102 and the sense transistor 104 to provide measurements of hydrogen concentration over a larger range than a single sense element might otherwise provide. The determination as to when to purge may be made by examining measurement outputs from the sense resistor 102 and/or the sense transistor 104. In the case of the sense resistor 102, the measurement output may be a particular resistance corresponding to the concentration of hydrogen gas in the environment of the sensor 100. Such a determination may be made by external circuitry and may be used to control the temperature control module 108.

FIG. 2 is a block diagram illustrating a top view of a single-chip hydrogen-sensing device 300, according to a preferred embodiment of the present invention. The device 300 includes a first sense resistor 302a, a second sense resistor 302b, and a third sense resistor 302c, to sense hydrogen concentrations at approximate first minimum concentrations and approximate first maximum concentrations. A first sense transistor 304a, a second sense transistor 304b, and a third sense transistor 304c may be used to sense hydrogen levels at second minimum concentrations and second maximum concentrations.

A temperature sensing diode 306 is used to determine the temperature of the device 300. A first heater Field Effect Transistor (FET) 308a and a second heater FET 308b are used to control the temperature of the device 300, so that the approximate temperature is 80 degrees Celsius during a hydrogen-sensing period and approximately 100 degrees Celsius during a purge period. The temperature sensing diode 306 and the heater FETs 308a–b are used in conjunction with external circuitry (not shown) to provide temperature regulation.

The sense resistors 302a–c, the sense transistors 304a–c, the temperature sensing diode 306, and the heater FETs 308a–b are located in and/or on a bulk semiconductor substrate 310. Additional layers may be present on the substrate 310, and are not shown in FIG. 2. For example, conductive and/or non-conductive layers may be deposited on one or more portions of the substrate 310. A series of left-side contacts 312 extend generally down the left side of the device and may be used to provide power, to receive measurements, and/or to control device operation. Similarly, right-side contacts 314 may be used to provide these same operations. In addition, the left-side contacts 312 and the right-side contacts 314 may be used for other functions, such as for testing the device 300. Special test elements, such as the test element 316 (and others resembling test element 316), may be located in or on the device 300 to enable verification that the device 300 is operating properly. An interconnection network 318 connects various components within the device 300. Most of the unreferenced components shown in FIG. 2 are test elements and/or interconnections between various referenced and unreferenced components.

The device 300 includes multiple sense resistors 302a–c, sense transistors 304a–c, and heater FETs 308a–b in order to provide redundancy. This enables the device 300 to operate in case one of the sensing mechanisms fails, and also enables improved accuracy due to more than one sensing element providing measurements and the ability to cross-check measurements. Other quantities of components within the device 300 may also be used without departing from the scope of the present invention.

The sense resistors 302a–c and the gates of the sense transistors 304a–c preferably include an alloy that resists the formation of a hydride phase of a catalytic metal contained in the alloy. The preferred alloy is a nickel and palladium alloy (PdNi). For example, an alloy of about 8% to 20% (by atom percentage) nickel (with the balance being palladium) may be used. Other alloy compositions and/or materials may also be used.

PdNi is not typically used in semiconductor manufacturing. In typical silicon fabrication facilities, metal films are first blanket-deposited across the entire wafer and are subsequently patterned by an etch process. Conventional etchants for PdNi, however, also attack various interconnect metals, such as aluminum, which would likely destroy the sensor. Likewise, use of an adhesion promoting layer (such as chromium) under the sense-resistive layer, to prevent problems during a lift-off process, may affect the sense transistors 304a–c. Thus, instead of using aluminum (or other similar metals) for an interconnect, and instead of using a lift-off process with an adhesion-promoting layer, the present invention uses a blanket-deposition and etching process. To avoid the undesirable effects caused by etchants on aluminum interconnects, an interconnect material capable of surviving subtractive etching is used. According to various embodiments of the present invention, the interconnect material is the same material used for hydrogen sensing. Thus, if a PdNi alloy is used for the sense resistors 302a–c, then a similar or identical material may be used for the interconnect metallizations. The alloy composition may be varied to improve conductivity and/or other characteristics. Use of an identical alloy, may, however have economic and efficiency advantages. The interconnect metallization is preferably covered with an oxide or nitride to make the interconnect metallization inert. Alternatively, any other material that is impervious to the etchant used may also serve as the interconnect metallization material. Gold, for example, may be used for the interconnect metallization material. Advantages in cost and yield might be realizable through the use of the hydrogen sensing material (PdNi) for the interconnect metallizations, since it is possible to use a single patterning process for both the sensing elements and the interconnect metallizations.

Silicided contacts are preferably used to provide contacts between the interconnect metallizations and various components, such as to the sources and drains of the sense transistor and the heater FET used in the temperature control module. Ideally, each silicided contact serves as an ohmic contact, such that the potential difference across the contact is proportional to the current passing through. As was described above with reference to FIG. 1, metals such as cobalt, titanium, tungsten, platinum, tantalum, and molybdenum, may be used to make silicided contacts. Other silicides may also be used. As an alternative, other materials providing a low resistance contact between a base layer (such as doped silicon) and an interconnect metallization may also be used. In another alternative embodiment, a silicide is also or alternatively used to implement all or a portion of the interconnect metallizations.

Figure 3:
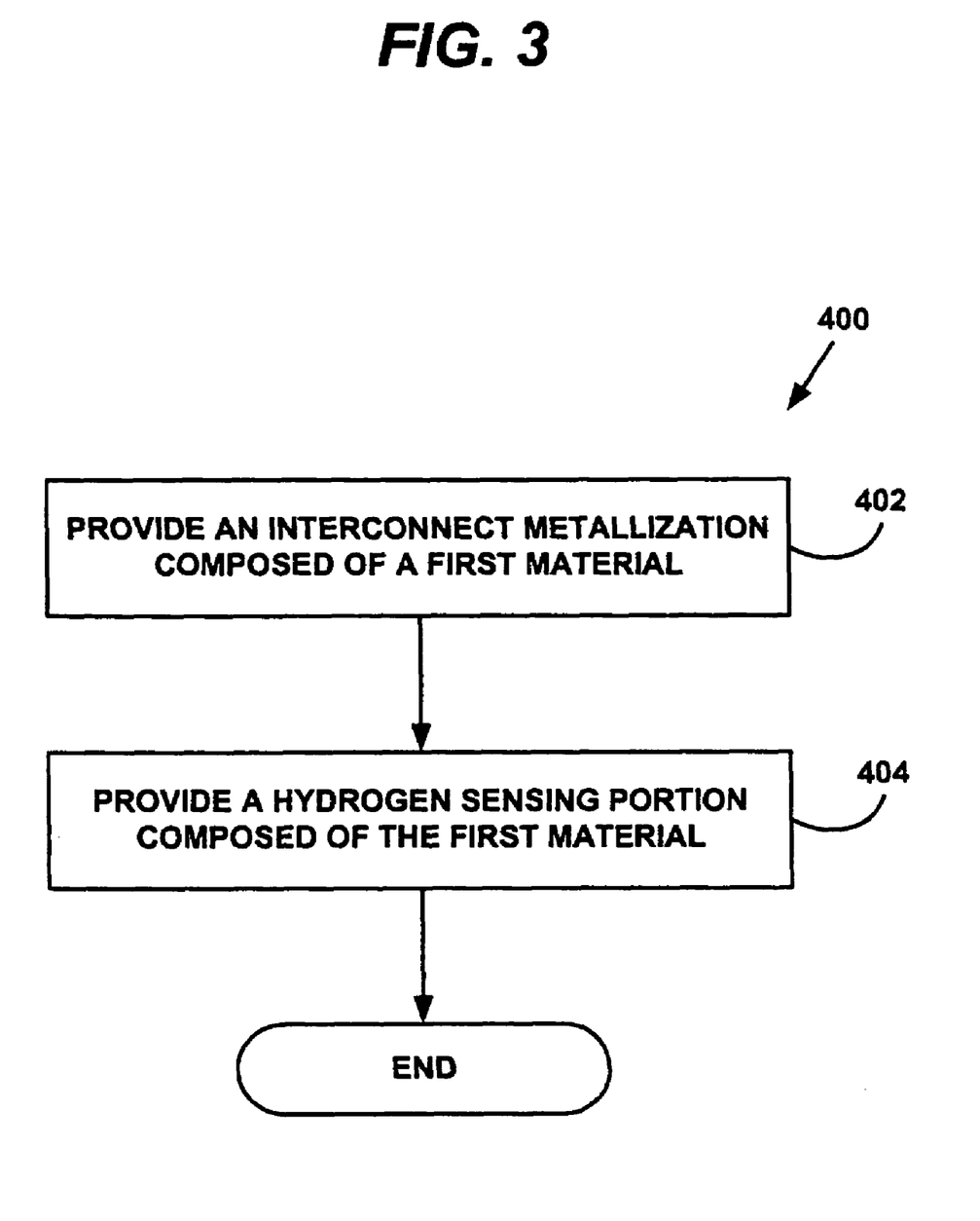
FIG. 3 is a flow diagram illustrating a method for fabricating a robust single-chip hydrogen sensor according to an embodiment of the present invention.

FIG. 3 is a flow diagram illustrating a method 400 for fabricating a robust single-chip hydrogen sensor, according to an embodiment of the present invention. In step 402, an interconnect metallization composed of a first material is provided. In step 404, a hydrogen sensing portion, also composed of the first material, is provided. The first material is preferably a PdNi alloy. The interconnect metallization is preferably covered with an oxide or nitride to make the interconnect metallization inert. The hydrogen sensor itself is preferably a single-chip sensor comprising a bulk silicon substrate, temperature control means, at least one sense transistor, and at least one sense resistor.

Figure 4:
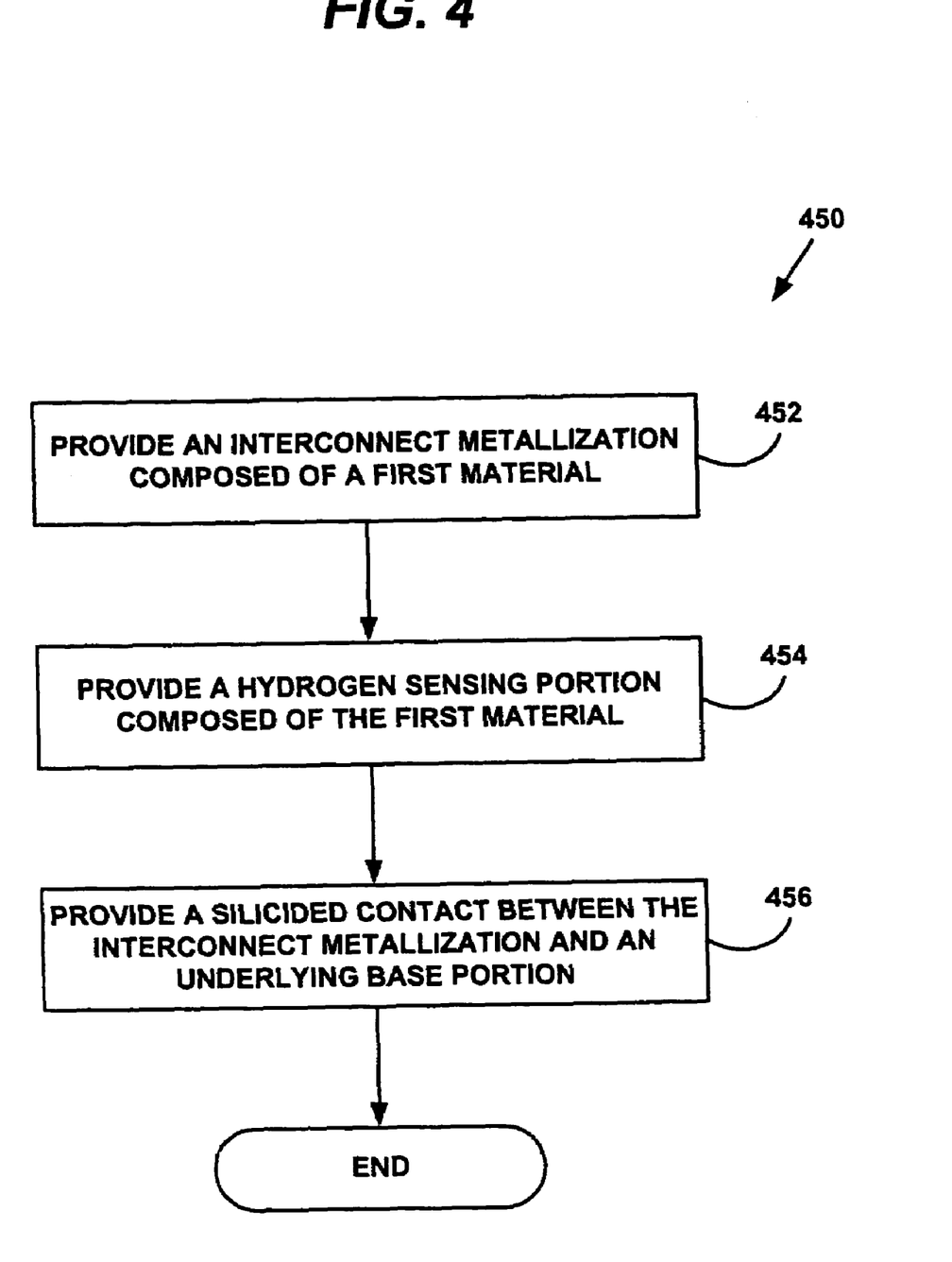
FIG. 4 is a flow diagram illustrating a method for fabricating a robust single-chip hydrogen sensor according to an embodiment of the present invention.

FIG. 4 is a flow diagram illustrating a method 450 for fabricating a robust single-chip hydrogen sensor, according to an embodiment of the present invention. Steps 452 and 454 correspond to steps 402 and 404 of the method 400. In step 456, a silicided contact is provided between the interconnect metallization and an underlying base portion. As was the case for the method 400, the interconnect metallization is preferably covered with an oxide or nitride to make the interconnect metallization inert. Preferably, the silicided contact may be provided by masking the underlying base portion, etching a contact portion from the masked underlying base portion, depositing a contact material, masking the contact material, and centering the contact material. The contact material is preferably one of the following: cobalt, titanium, tungsten, platinum, tantalum, and molybdenum.

Figure 5:
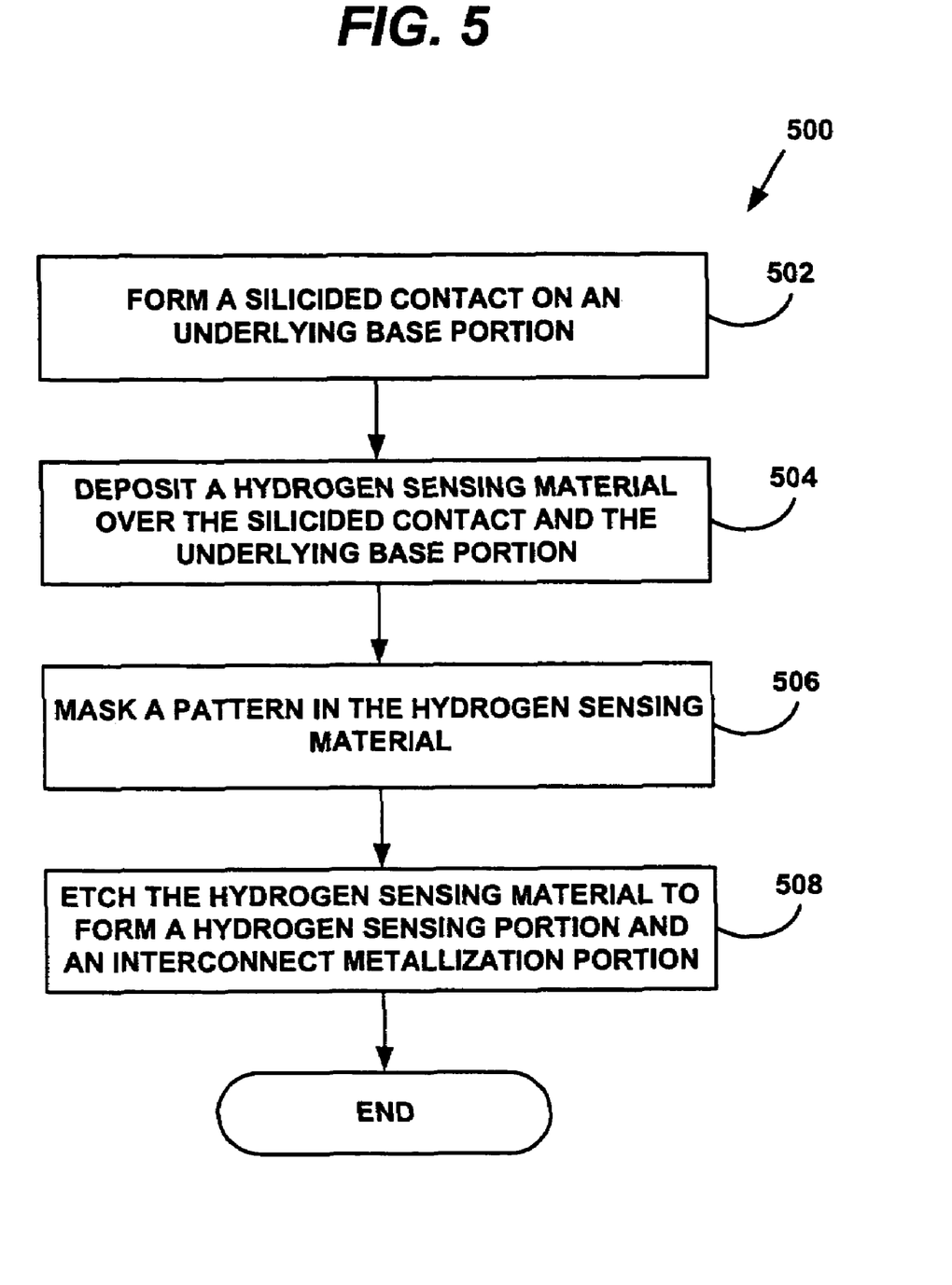
FIG. 5 is a flow diagram illustrating a method for fabricating a robust single-chip hydrogen sensor according to an embodiment of the present invention.

FIG. 5 is a flow diagram illustrating a method 500 for fabricating a robust single-chip hydrogen sensor, according to an embodiment of the present invention. In step 502, a silicided contact is formed on an underlying base portion. In step 504, a hydrogen sensing material is deposited over the silicided contact and the underlying base portion. In step 506, a pattern is masked in the hydrogen sensing material. In step 508, the hydrogen sensing material is etched to form a hydrogen sensing portion and an interconnect metallization portion. Forming the silicided contact preferably involves depositing, etching, and centering one of the following materials: cobalt, titanium, tungsten, platinum, tantalum, and molybdenum. The interconnect metallization is preferably covered with an oxide or nitride to make the interconnect metallization inert. The underlying base portion preferably is one of the following: a semiconductor substrate, a conductive layer, a semiconductor layer, or a non-conductive layer.

Figure 6:
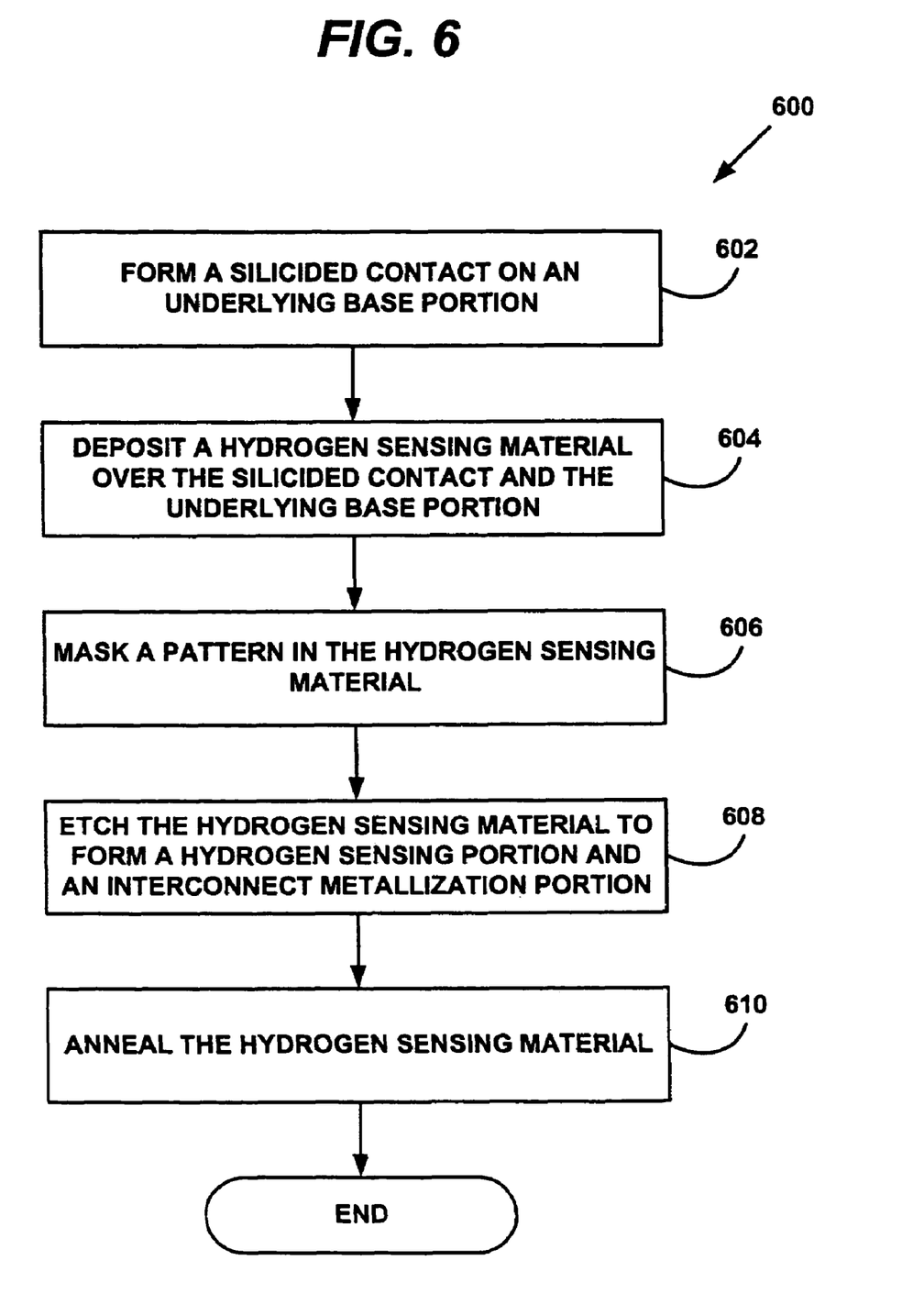
FIG. 6 is a flow diagram illustrating a method for fabricating a single-chip hydrogen sensor, according to an embodiment of the present invention.

FIG. 6 is a flow diagram illustrating a method 600 for fabricating a robust single-chip hydrogen sensor, according to an embodiment of the present invention. Steps 602–608 correspond respectively to steps 502–508 in the method 500. In step 610, the hydrogen sensing material is annealed, using any well known annealing process. As was the case for the method 500, the interconnect metallization is preferably covered with an oxide or nitride to make the interconnect metallization inert.

TABLE 1 illustrates process steps that may be used to produce the single-chip hydrogen-sensing device 300, according to a preferred embodiment of the present invention. The steps are preferably performed in order, from top-to-bottom, starting with the left column. The abbreviations correspond primarily to semiconductor processing steps. Such abbreviations should be readily apparent to those having skill in the relevant technology field.

TABLE 1

| | | |
|---|---|---|
| Phos. Implant | poly etch | nitride 2 mask |
| initial ox | spacer ox | nitride dry etch |
| diff mask | n+ mask | BPSG |
| diff etch | n+ imp | BPSG reflow |
| p-well mask | s/d implant | contact mask |
| p-well imp | poly re-ox | contact etch |
| chan-stop imp | p+ mask | Co dep |
| p-well drive | p+ implant | Co sinter |
| nitride strip | BF2 implant | Co etch |
| threshold imp | h-gate mask | Alloy |
| gate ox | h-gate implant split | NiPd dep |
| poly dep | boe etchback | NiPd mask |
| poly dope | h-gate oxidation 200A | NiPd etch |
| poly mask | R&D nitride dep 200A | Anneal |

In Table 1, the last few steps (involving Co and NiPd) refer to making silicided contacts (cobalt silicide) and a combination NiPd interconnect metallization and sensing structure. The mask and etch steps performed prior to the cobalt deposition serve to confine the cobalt (and the cobalt silicide resulting after sintering) to the desired contact location. Other silicides (or other contact materials) may be formed in a similar manner. It should be noted that although Table 1 describes using only one NiPd deposition, mask, and etch process to form both the interconnect metallization and the sensing structure, a separate deposition, mask, and etch process could also be performed. For example, a separate deposition, mask, and etch process would be required if the interconnect metallization material was different from the hydrogen sensing material.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

The claims should not be read as limited to the described order or elements unless stated to that effect. In addition, use of the term "means" in any claim is intended to invoke 35 U.S.C. §112, paragraph 6, and any claim without the word "means" is not so intended. Therefore, all embodiments that come within the scope and spirit of the following claims and equivalents thereto are claimed as the invention.

What is claimed is:

1. A method for fabricating a single-chip hydrogen sensing-device, comprising in combination:
   forming a silicided contact on an underlying base portion;
   depositing a hydrogen sensing material over the silicided contact and the underlying base portion;
   masking a pattern in the hydrogen sensing material; and
   etching the hydrogen sensing material to form a hydrogen sensing portion and an interconnect metallization portion.

2. The method of claim 1, further comprising annealing the hydrogen sensing material.

3. The method of claim 1, further comprising covering the interconnect metallization portion with a material selected from the group consisting of an oxide and a nitride.

4. The method of claim 1, wherein forming the silicided contact comprises depositing, etching, and sintering a first material selected from the group consisting of cobalt, titanium, tungsten, platinum, tantalum, and molybdenum.

5. The method of claim 1, wherein the underlying base portion includes at least one component selected from the group consisting of a semiconductor substrate, a conductive layer, a semiconductor layer, and a non-conductive layer.

* * * * *